(12) United States Patent
Appelo et al.

(10) Patent No.: US 7,725,268 B2
(45) Date of Patent: May 25, 2010

(54) SENSING MODULE AND METHOD FOR GAS CONCENTRATION MEASUREMENT

(75) Inventors: Roger Marcel Appelo, Beilen (NL); Tom Urban Artursson, Almelo (NL); Per Anders Holmberg, Almelo (NL); Nicolae Barsan, Almelo (NL); Heiko Eugen Ulmer, Almelo (NL)

(73) Assignee: Sensata Technologies Holland B.V. (NL)

( * ) Notice: Subject to any disclaimer, the term of this patent is extended or adjusted under 35 U.S.C. 154(b) by 190 days.

(21) Appl. No.: 11/791,459

(22) PCT Filed: Nov. 25, 2004

(86) PCT No.: PCT/NL2004/000813

§ 371 (c)(1),
(2), (4) Date: Oct. 15, 2007

(87) PCT Pub. No.: WO2006/057549

PCT Pub. Date: Jun. 1, 2006

(65) Prior Publication Data

US 2008/0051021 A1 Feb. 28, 2008

(51) Int. Cl.
*G06F 19/00* (2006.01)
*G06F 7/00* (2006.01)
*B60H 1/00* (2006.01)

(52) U.S. Cl. ............................ 702/23; 701/103; 454/75

(58) Field of Classification Search .................. 702/23; 340/632; 73/1.03
See application file for complete search history.

(56) References Cited

U.S. PATENT DOCUMENTS

| 6,112,161 A | 8/2000 | Dryden et al. |
| 6,298,291 B1 | 10/2001 | Davis, Jr. et al. |
| 6,526,801 B2 * | 3/2003 | Kouznetsov et al. ......... 73/1.03 |
| 2002/0121126 A1 | 9/2002 | Kouznestov et al. |
| 2005/0282483 A1 * | 12/2005 | Inoue et al. ................... 454/20 |

FOREIGN PATENT DOCUMENTS

WO    WO 2004/048137 A1    6/2004

* cited by examiner

*Primary Examiner*—Bryan Bui
(74) *Attorney, Agent, or Firm*—Russell E. Baumann

(57) ABSTRACT

Method and sensing module for sensing pollution of outside air. The sensing module (1) comprises an electro chemical sensing element (3), and a processor (2). A sensing module output signal is provided based on the measurement signal and a baseline signal level. The baseline signal level is adapted depending on two threshold levels (13-15). A pollution concentration value is determined from the measurement signal and a classification level of air pollution is provided as sensing module output signal. A classification level is determined using a plurality of classification threshold values and the pollution concentration values. The plurality of classification threshold values are dynamically adjustable.

9 Claims, 2 Drawing Sheets

SENSING MODULE AND METHOD FOR GAS CONCENTRATION MEASUREMENT

The present application is a U.S. National Phase Application of International Application No. PCT/NL2004/000813 (filed Nov. 25, 2004) which is hereby incorporated by reference in its entirety.

FIELD OF THE INVENTION

The present invention relates to a sensing module for sensing pollution of outside air, such as CO, hydrocarbons, NOx, or Volatile Organic Compounds. The sensing module comprises at least one electro chemical sensing element, and a processor for processing a measurement signal of the at least one electro chemical sensing element, the processor being arranged to provide a sensing module output signal based on the measurement signal and a baseline signal level.

PRIOR ART

A gas sensor arrangement for detecting pollutants is disclosed in European patent EP-B-0 750 191. Two sensor elements are used, one specifically sensitive to oxidizing gasses, and one specifically sensitive for reducing gasses, arranged in a voltage divider arrangement.

A sensor arrangement for controlling vehicle ventilation systems is disclosed in European patent EP-B-0 757 632. The sensor arrangement is arranged to control a ventilation system in a vehicle based on the concentration of pollutants in the air. The sensor arrangement is chosen such that both oxidizing (reducable) and reducing (oxidizable) gasses may be detected using a single sensor element. As a result of processing differentiated signals in time of the single sensing element, both exhaust fumes of diesel engines and petrol engines are reliably detected. According to this publication, the outside ventilation is also interrupted when the absolute value of the sensor signal is outside predetermined threshold levels.

European patent application EP-A-1 256 470 describes a sensor arrangement for controlling a vehicle ventilation system, in which the sensor sensitivity is dependent on a number of parameters. The parameters comprise the number of occupants of the vehicle, the inside temperature, the inside humidity, the vehicle speed, and the settings of an air conditioning unit in the vehicle.

SUMMARY OF THE INVENTION

The present invention seeks to provide a sensing module for sensing pollution in air, which has improved characteristics over prior art systems.

According to the present invention, a sensing module according to the preamble defined above is provided, in which the processor is further arranged to adapt the baseline signal level with a first baseline adaptation value when the measurement signal is lower than a first threshold level, and to adapt the baseline signal level with a second baseline adaptation value when the measurement signal is higher than the first threshold level and lower than a second threshold level, and to adapt the baseline signal level with a third baseline adaptation value when the measurement signal is higher than the second threshold level. By dynamically amending the baseline signal level, it is possible to provide a more useful and reliable output signal (in the form of an absolute concentration measurement), which may e.g. be used to control a car ventilation system. It is noted that in general two sensing elements are used for absolute concentration measurement of multiple pollutants (oxidizing and reducing gasses).

In a further embodiment of the present invention, the absolute value of the first baseline adaptation value is higher than the absolute value of the second baseline adaptation value, which in turn is higher than the absolute value of the third baseline adaptation value. This allows to use the first baseline adaptation value to correct cross sensitivity of the sensing module fast while the other baseline adaptation values are used to correct drift.

In further embodiments, the first threshold value and second threshold value are adjustable. According to circumstances, but also according to the specific characteristics of the sensing elements, the threshold values may be adjusted, providing a very flexible sensing module suited for varying applications.

Also, in a further embodiment, the first, second, and third baseline adaptation values are adjustable. With these adjustments, the rate of adaptation of the sensing module to high or low concentrations of pollutants may be fine tuned, resulting in an even more flexibly applicable sensing module.

The processor may, in a further embodiment, be arranged for calculating a pollution concentration value from the measurement signal and for providing a classification level of air pollution as sensing module output signal, in which the processor is arranged to determine a classification level using a plurality of classification threshold values and the pollution concentration value, and in which the plurality of classification threshold values are dynamically adjustable.

The processor may further be arranged to determine a rate of classification threshold crossings for at least one of the classification threshold values, and to adjust at least one of the plurality of classification threshold values upward (i.e. to obtain a lower sensitivity of the sensing module) when the determined rate is above a first predetermined value, and downward (i.e. to obtain a higher sensitivity) when the determined rate is below a second predetermined value. Advantageously, classification threshold crossings of a very short duration (i.e. shorter than a predetermined time duration), are not taken into account. This embodiment allows to dynamically adapt the sensitivity of the sensing module, which will result in a better, more efficient control of the vehicle ventilation system when driving in various circumstances.

In a further embodiment, the sensing module is arranged to determine the concentration of both oxidizable gasses, such as CO or hydrocarbons, and reducable gasses, such as NOx. This may be accomplished using two sensing elements which are specifically sensitive for one of the types of gasses, or by using a sensing element, or sensing element arrangement, which allows to determine the concentration of both types of gasses. Of course, further sensing elements may be used to make the sensing module suitable for detecting other types of pollutants, such as volatile organic compounds.

The processor may in a further embodiment, be arranged to predict a final concentration value based on a rising slope of measured values in a predetermined time period, and to adjust the threshold values according to the predicted final concentration value. This will allow a faster classification output, and a more accurate functioning of the sensing module for obtaining absolute concentration values and/or correct pollution classification.

In a further aspect, the present invention relates to a vehicle ventilation system, in which supply of outside air to an inner space of the vehicle is controlled using a ventilation controller, the ventilation controller being arranged to interface with a sensing module according to the present invention. The ventilation controller may be arranged to receive absolute concentration measurements of pollutants and control the ventilation system, or levels of pollutants as classified by the sensing module.

In an even further aspect, the present invention relates to a method for sensing pollution of outside air using at least one electro chemical sensing element, comprising processing a measurement signal of the at least one electro chemical sensing element, providing a sensing output signal based on the measurement signal and a baseline signal level, and adapting the baseline signal level with a first baseline adaptation value when the measurement signal is lower than a first threshold level, adapting the baseline signal level with a second baseline adaptation value when the measurement signal is higher than the first threshold level and lower than a second threshold level, and adapting the baseline signal level with a third baseline adaptation value when the measurement signal is higher than the second threshold level. Further embodiments of the present method are described in the dependent method claims.

SHORT DESCRIPTION OF DRAWINGS

The present invention will be discussed in more detail below, using a number of exemplary embodiments, with reference to the attached drawings, in which FIG. 1 shows a schematic diagram of an embodiment of a sensing module according to the present invention;

DETAILED DESCRIPTION OF EXEMPLARY EMBODIMENTS

Electro chemical sensing elements are used presently for detecting pollution in air, such as oxidizable gasses (CO, $CH_x$, ...) and reducable gasses (NO, $NO_x$, ...). These kind of sensing elements may be used to control the ventilation system of a vehicle, such as a passenger car. More general, such sensing elements are used in heating, ventilation and air conditioning systems (HVAC). When pollution occurs in outside air, e.g. when entering a badly ventilated tunnel filled with exhaust fumes, the air vent of the vehicle may be closed off (internal air circulation).

Figure 1:
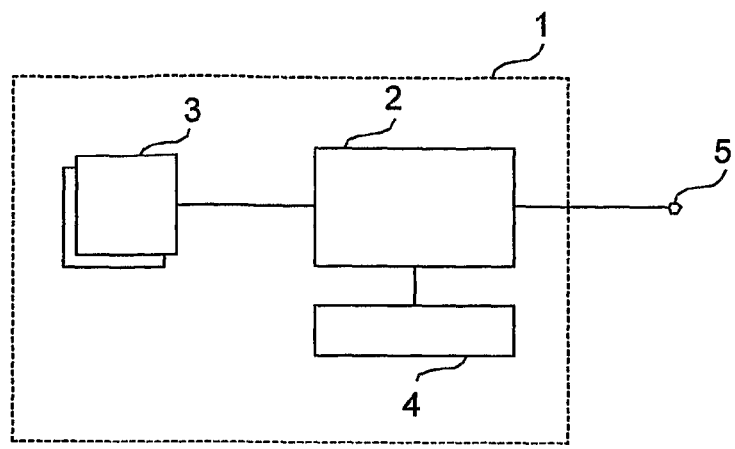

In FIG. 1, a schematic diagram is shown of a sensing module 1 for use in a vehicle ventilation system. The sensing module 1 comprises one or more sensing elements 3, which are connected to a processor 2. The processor 2 may be a dedicated electronic circuit which processes the signals from the sensing elements 3 (analog or digital circuitry, or a combination of both), or may be in the form of a general purpose processing unit 2 connected to a memory 4 (e.g. an integrated memory). The memory 4, e.g. in the form of semiconductor memory units, may comprise (software) program instructions which control the functioning of the processing unit 2. The processor 2 is arranged to provide an output signal 5, which may be transferred to the vehicle ventilation system (not shown) for controlling the operation thereof.

The sensing elements 3 are usually electro chemical sensing elements, which comprise a sensing material of which a physical property, such as its resistance, changes under the influence of the concentration of certain compounds in the ambient air around the sensing element 3. The sensing elements 3 may be especially suited for detecting oxidizable gasses, such as CO and hydrocarbons, reducable gasses, such as NO and $NO_x$, and other compounds, e.g. volatile organic compounds (VOC). Volatile organic compounds may e.g. originate from manure, compost or asphalt. When these compounds or gasses are present in the ambient air of a vehicle, the normal operation of the vehicle's ventilation system would allow these to enter the vehicle interior, which can be unpleasant or even dangerous for the occupants of the vehicle. Thus these sensors are normally used to shut of the external air intake when too high a concentration of any of these compounds is detected.

Due to the physical nature of the sensing elements 3, the output signal of the sensing elements is not only dependent on the concentration of the compounds to be detected, but also dependent on other physical parameters, such as temperature, age of the sensing element 3, etc. This results in a drift of a baseline signal level, i.e. the sensing element 3 output signal in clean air. Normally, this drift would require a frequent calibration of the sensing elements 3, or the use of relative measurements to only detect a relative increase in e.g. the CO concentration of the outside air. The calculation of this baseline value and its comparison to sensor signal allows the prediction of absolute gas concentrations.

Figure 2:
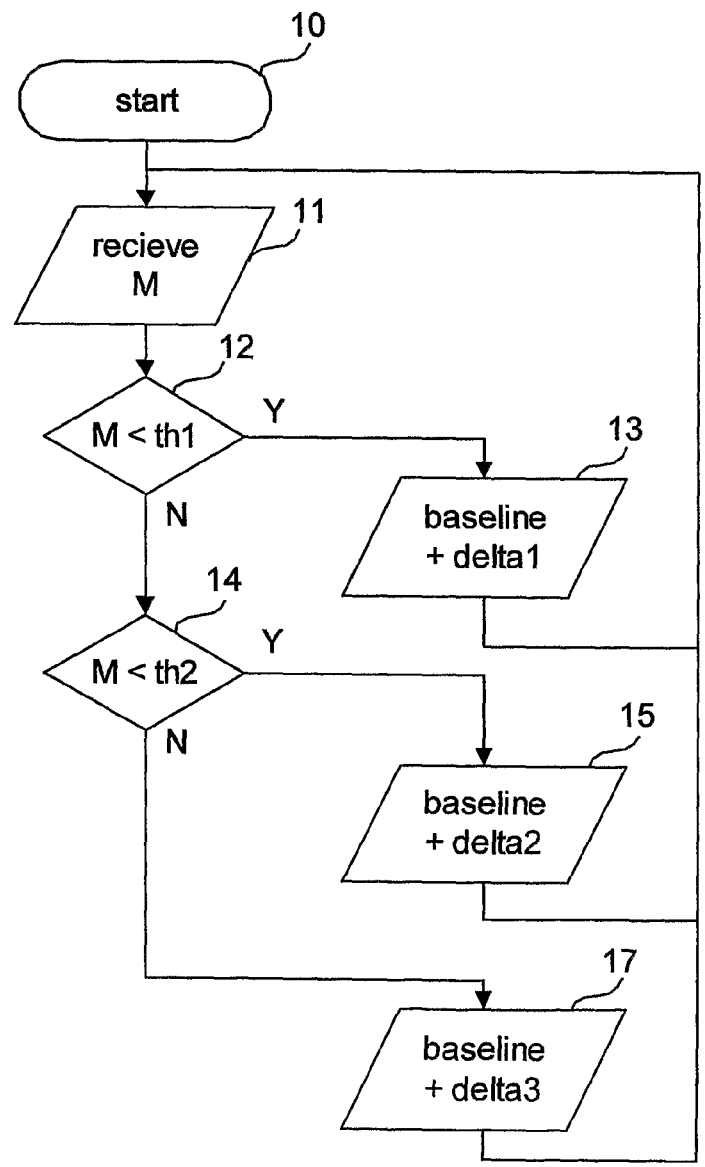
FIG. 2 shows a flow chart of a first embodiment of processing in the sensing module of FIG. 1.

In a first embodiment of the present invention, the processor 2 is arranged to adapt the baseline signal level of each of the sensing elements 3 which are present in the sensing module 1, according to the flow chart as given in FIG. 2. Each time a measurement value of a sensing element 3 becomes available (e.g. with a clock frequency under control of the processor 2), the processor 2 receives the measurement value M in block 11. In decision block 12, the received measurement value M is compared to a first threshold level th1 (e.g. stored in memory 4), and when the measurement value M is below the first threshold value, the baseline signal level is adapted with a first delta value delta1 (which may be positive or negative) in block 13, and the process returns to block 11. In decision block 14, the received measurement value M is compared to a second threshold level th2 (e.g. also stored in memory 4), and when the measurement value M is lower than the second threshold value th2, the baseline signal level is adapted with a second delta value delta 2 in block 15, and the process returns to block 11. In the other branch output of decision block 14 (when the measurement value M is over the second threshold value th2), the baseline signal level is adapted with a third delta value delta3 (which may be positive or negative) in block 17 and the process returns to block 11.

In summary, the process performs the following adaptations using two threshold values th1, th2:

| | |
|---|---|
| if M<th1 then | baseline = baseline + delta1 |
| elseif th1<M<th2 then | baseline = baseline + delta2 |
| else | baseline = baseline + delta3 |

In absolute value, delta1 is larger than delta2, which again is larger than delta3 (|delta1|>|delta2|>|delta3|). In an exemplary embodiment, delta1 is always negative and delta2 and delta3 are always positive, e.g. when th1=0. The (absolute) first delta value delta1 is much larger than the second delta value delta2 and the third delta value delta3. This has the result that the baseline signal level is adapted quickly and strongly when the measurement value M is below the first threshold value th1. On the other hand, when the measurement value M is above the second threshold value th2, the baseline signal level is adapted more slowly using the smallest delta value delta3. In between the two threshold values th1, th2, the baseline signal level is adapted with a moderate value delta2. This allows a more optimal performance of the sensing module 1. The difference between the actual measurement value of a sensing element 3 and its corresponding baseline signal level may provide an output 5 of the sensing module 1 with a gas concentration with a stable baseline.

The threshold values th1, th2 are tunable to the specific sensing elements 3 used, and the use of the sensing module 1 as a whole. Also, the adaptation values delta1, delta2 are tunable to the specific circumstances of use. These values th1, th2, delta1, delta2 may e.g. be stored in the memory 4. Alternatively, these values th1, th2, delta1, delta2 may be adjusted during operation of the sensing module 1.

In a further advantageous embodiment, the sensing module 1 provides a classification of the pollution level as output signal. The classification output may be dependent on which type of pollution is measured by the sensing elements 3 of the sensing module 1. Multiple sensing elements 3 may be used, and a model of the sensing elements 3, by the processor 2 to calculate absolute concentrations of different types of pollutants. In table 1 below, such a classification example is shown.

TABLE 1

| CO/HC | $NO_x$ |
|---|---|
| Level 0 | Level 0 |
| 0-4 ppm | 0-200 ppb |
| Level 1 | Level 1 |
| 4-12 ppm | 200-500 ppb |
| Level 2 | Level 2 |
| 12-30 ppm | >500 ppb |
| Level 3 | |
| >30 ppm | |

Figure 4:
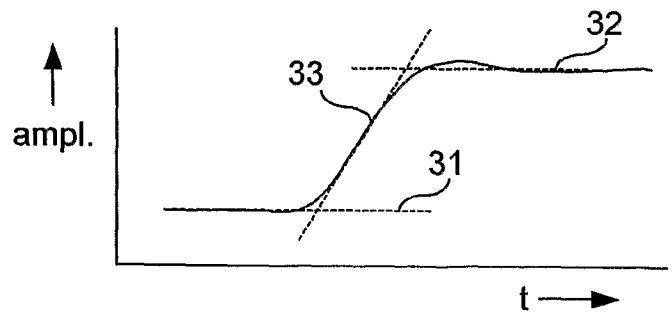
FIG. 4 shows a plot of a signal value in the sensing module over time.

In an even further embodiment of the present invention, the response of the sensing module 1 of the earlier described embodiments may be improved. For this, the processor 2 is arranged to predict a final value of the signal of a sensing element 3 (or a final value of the determined concentration level). When e.g. the concentration of volatile organic components in the environment of a vehicle changes (e.g. when driving past a field with freshly deposited manure), the response of the sensing element 3 will change from an initial value (indicated by reference numeral 31 in the signal plot of FIG. 4) to a final value (indicated by reference numeral 32). The signal value in between the initial value and final value will have a certain slope 33, which in general is determined by the initial and final value. The processor 2 is arranged to predict the final value 32 based on the initial value 31 and the slope 33. Using this predicted final value, the processor 2 may already adapt various system parameters, e.g. the baseline signal value (see flow chart of FIG. 2). Also, this predicted final value may be used to provide an anticipated classification. As a result, the sensing unit 1 may be fine tuned more accurately, at the cost of a slightly increased processing cost.

Figure 3:
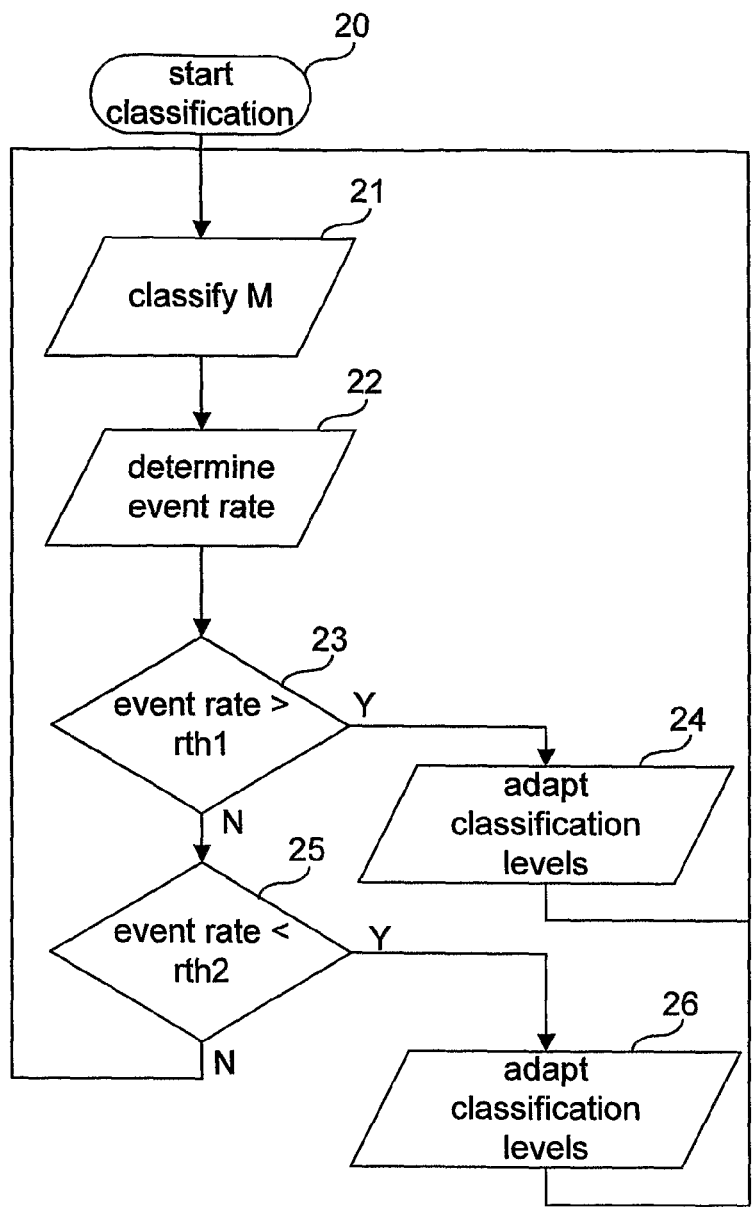
FIG. 3 shows a flow chart of a second embodiment of processing in the sensing module of FIG. 1.

The processor 2 is arranged to provide the highest level of any of the measured pollutants as output signal 5 of the sensing module 1. In an embodiment of the present invention, which may be applied as such, the boundaries of the various levels are adaptable. This is particularly useful in an automotive environment, where the environmental conditions may vary over a broad range (e.g. city atmosphere, rural atmosphere, tunnel atmosphere, . . . ). The processor 2, in this embodiment, is arranged to perform the process as depicted in the flow chart of FIG. 3. After the start of the classification process (block 20), the processor 2 receives a measurement value M (or a set of measurement values, e.g. concentration of both CO/HC and $NO_x$), and classifies (block 21) the measurement value according to a table stored in memory 4 (e.g. corresponding to table I). In block 22, the processor 2 updates an event rate, which e.g. is equal to the number of classification threshold crossings (for at least a minimum predetermined duration) in a given time period. Threshold crossings which are very short are not taken into account, to prevent false transitions and to make the method more robust. When the event rate is higher than a first event rate threshold rth1 (block 23), this may indicate a very polluted environment, and accordingly, the sensitivity of the sensing module 1 may be set lower. This may be accomplished by adapting one or more of the classification threshold values to a higher value (block 24). In an analogue manner, it is checked in block 25 whether the number of classification thresholds in a given time period is below a second rate threshold rth2. If this is the case, the sensing module 1 may revert to a more sensitive state, e.g. by lowering one or more of the classification threshold values in table I (block 25). After adaptation of the classification levels, the processor 2 returns to block 21 for classifying the next measurement M. Adaptation of the classification threshold levels may also be accomplished by changing to one of a plurality of classification tables like table I, which may e.g. be stored in the memory 4.

The invention claimed is:

1. Sensing module for sensing pollution of outside air, the sensing module (1) comprising at least one electro chemical sensing element (3), and a processor (2) for processing a measurement signal of the at least one electro chemical sensing element (3), the processor (2) being arranged to provide a sensing module output signal based on the measurement signal and a baseline signal level, and configured to perform for each received measurement value the following operation:
   adapting the baseline signal level with a first baseline adaptation value when the measurement value is lower than a first threshold level;
   adapting the baseline signal level with a second baseline adaptation value when the measurement value is higher than the first threshold level and lower than a second threshold level; and
   adapting the baseline signal level with a third baseline adaptation value when the measurement value is higher than the second threshold level.

2. Sensing module according to claim 1, in which the absolute value of the first baseline adaptation value is higher than the absolute value of the second baseline adaptation value, which in turn is higher than the absolute value of the third baseline adaptation value.

3. Sensing module according to claim 1, in which the first threshold value and second threshold value are adjustable.

4. Sensing module according to claim 1, in which the first baseline adaptation value, second baseline adaptation value and third baseline adaptation value are adjustable.

5. Sensing module according to claim 1, in which the processor (2) is arranged for calculating a pollution concentration value from the measurement signal and for providing a classification level of air pollution as sensing module output signal, in which the processor (2) is arranged to determine a classification level using a plurality of classification threshold values and the pollution concentration value, and in which the plurality of classification threshold values are dynamically adjustable.

6. Sensing module according to claim 5, in which the processor (2) is further arranged to determine a rate of classification threshold crossings for at least one of the classification threshold values, and to adjust at least one of the plurality of classification threshold values upward when the determined rate is above a first predetermined value, and downward when the determined rate is below a second predetermined value.

7. Sensing module according to claim 1, in which the sensing module (1) is arranged to determine the concentration of both oxidizable gasses, such as CO or hydrocarbons, and reducable gasses, such as NOx.

8. Sensing module according to claim 1, in which the processor (2) is arranged to predict a final concentration value (32) based on a rising slope (33) of measured values in a predetermined time period, and to adjust the threshold values according to the predicted final concentration value (32).

9. Vehicle ventilation system, in which supply of outside air to an inner space of the vehicle is controlled using a ventilation controller, the ventilation controller being arranged to interface with a sensing module (1) according to claim 1.

\* \* \* \* \*